United States Patent
Billodeaux et al.

(10) Patent No.: US 12,152,005 B2
(45) Date of Patent: Nov. 26, 2024

(54) PROCESSES FOR PRODUCING CARBOXYLIC ACIDS

(71) Applicant: EASTMAN CHEMICAL COMPANY, Kingsport, TN (US)

(72) Inventors: Damon Ray Billodeaux, Longview, TN (US); Kenneth Wayne Hampton, Jr., Gilmer, TX (US); Magnus Alexander Pauly, Raleigh, NC (US)

(73) Assignee: Eastman Chemical Company, Kingsport, TN (US)

( * ) Notice: Subject to any disclaimer, the term of this patent is extended or adjusted under 35 U.S.C. 154(b) by 493 days.

(21) Appl. No.: 17/441,726

(22) PCT Filed: Mar. 25, 2020

(86) PCT No.: PCT/US2020/024565
§ 371 (c)(1),
(2) Date: Sep. 22, 2021

(87) PCT Pub. No.: WO2020/205348
PCT Pub. Date: Oct. 8, 2020

(65) Prior Publication Data
US 2022/0185759 A1 Jun. 16, 2022

Related U.S. Application Data

(60) Provisional application No. 62/827,893, filed on Apr. 2, 2019.

(51) Int. Cl.
C07C 51/09 (2006.01)

(52) U.S. Cl.
CPC .................. C07C 51/09 (2013.01)

(58) Field of Classification Search
CPC ...................................... C07C 51/09
See application file for complete search history.

(56) References Cited

U.S. PATENT DOCUMENTS

| | | |
|---|---|---|
| 3,907,884 A | 9/1975 | Lynn et al. |
| 4,185,027 A | 1/1980 | Logan |
| 5,053,535 A | 10/1991 | Shima et al. |
| 5,440,061 A * | 8/1995 | Gibson ............ C11C 1/00 554/154 |
| 5,508,455 A | 4/1996 | Gibson |
| 5,872,289 A | 2/1999 | Appleby et al. |
| 6,525,218 B2 | 2/2003 | Kouno et al. |
| 2015/0166450 A1 | 6/2015 | Billodeaux et al. |

FOREIGN PATENT DOCUMENTS

| | | | |
|---|---|---|---|
| FR | 2701706 | 8/1994 | |
| JP | H06 84319 B2 * | 10/1994 | ............. C07C 1/148 |
| WO | WO 2007/028714 A2 | 5/2007 | |

OTHER PUBLICATIONS

JP H06 84319 B2, Sumitomo Chemical, Co., Removal of the esters and the hydrocarbons, English translation, 4 pages (Year: 1994).*
Tommila, E., et al., Effect of the solvent on reaction velocity. V. Acid hydrolysis of carboxylic esters n acetone-water mixtures , Annales Academiae Scientiarum Fennicae, Series A4: Chemica, No. 53, pp. 3-24, 1 page abstract (Year: 1954).*
Koskikallio, J., Kinetics of acid hydrolysis of ethyl acetate in dioxane-water mixtures and the esterification of acetic acid in dioxane-ethanol mixtures, Suomen Kemistilehti B, B35(No. 4) pp. 62-69, 1 page abstract (Year: 1962).*
Khalil, F. Y., et al., The role of dimethylsulphoxide as a solvent in the kinetics of the acid and alkaline hydrolysis of benzyl acetate, Bulletin Des Societes Chimiques Belges: Vlaamse Chemise Vereniging, vol. 91, No. 2, pp. 101-110 (Year: 1982).*
Vojtko, J., Determination of Organic Acid Structure Effect on the Equilibrium Constant of Esterification, Zeitschrift Fuer Physikalische Chemie, vol. 271, No. 6, pp. 1227-1235 (Year: 1990).*
J Vojtko: "Determination of Organic Acid Structure Effect on the Equilibrium Constant of Esterification", Zeitschrift Fuer Physikalische Chemie, vol. 271, No. 6, Jan. 1, 1990 (Jan. 1, 1990), pp. 1227-1235.
Fayez Y. Khalil et al: "The role of Dimethylsulphoxide as a Solvent in the Kinetics of the Acid and Alkaline Hydrolyses of Benzyl Acetate", Bulletin Des Societes Chimiques Belges: Vlaamse Chemise Vereniging, vol. 91, No. 2, Jan. 1, 1982 (Jan. 1, 1982), pp. 101-110.
Clea M. L. Frasson et al: "Solvent effect and proton inventory in the hydrolysis ofp-methylphenyl trichloroacetate", Journal of Physical Organic Chemistry., vol. 19, No. 2, Jan. 1, 2006 (Jan. 1, 2006), pp. 143-147.
Vydrin et al: "Acoustospectoscopic investigation of intermediate stages of chemical reactions. Hydrolysis of isobutyl acetate.", Russian Journal of Physical Chemistry A, vol. 64, No. 10, Jan. 1, 1990 (Jan. 1, 1990), pp. 1514-1517.
F.Y. Khalil et al: "Kinetics of the Acid Hydrolysis of Benzyl Acetate in Acetone-Water Mixtures", Zetischrift Fur Physikalische Chemie, vol. 75, No. 5_6, Sep. 1, 1971 (Sep. 1, 1971).
Hilton et al. "The Acid Catalyzed Hydrolysis of Ethyl Esters of Aliphatic Acids" JACS, 1941, vol. 63, pp. 3466-3469.

* cited by examiner

*Primary Examiner* — Yate' K Cutliff
(74) *Attorney, Agent, or Firm* — Steven A. Owen

(57) ABSTRACT

Processes are disclosed for preparing carboxylic acids from organic esters, the processes comprising contacting an ester with water in the presence of an acid catalyst and a homogenizing solvent at conditions effective to form a carboxylic acid. The homogenizing solvent is present in an amount sufficient to form a single-phase reaction mixture comprising the ester, water, and homogenizing solvent. The homogenizing solvent may be selected from acetonitrile, dimethyl sulfoxide, and 1,4-dioxane.

12 Claims, No Drawings

PROCESSES FOR PRODUCING CARBOXYLIC ACIDS

CROSS-REFERENCE TO RELATED APPLICATION(S)

This application is a national stage filing under 35 USC § 371 of International Application Number PCT/US2020/024565, filed on, Mar. 25, 2020 which claims the benefit of the filing date to U.S. Provisional Application No. 62/827,893, filed on Apr. 2, 2019, the entire disclosures of which are incorporated by reference herein.

FIELD OF THE INVENTION

The present invention is directed to processes for preparing carboxylic acids from organic esters.

BACKGROUND OF THE INVENTION

Production of carboxylic acids may be accomplished by the catalyzed or uncatalyzed oxidation of the corresponding aldehyde. The oxidation of the aldehyde results in the formation of peroxyacid, followed by the generation of an intermediate that can lead to production of two moles of the desired acid (Pathway A). However, in addition to the desired carboxylic acid, a co-product formate ester can be produced through the Bayer-Villager oxidation. (Pathway B). The formation of these formate esters, particularly in the case of isobutyric acid and 2-ethyl hexanoic acid, is a significant financial burden on commercial carboxylic acid plants through the loss of raw material—both to yield loss and loss of recoverable aldehyde from co-distillation with the close boiling ester—as well as costs associated with incineration of the low value ester. In view of problems associated with low selectivity of aldehyde oxidation, it would be beneficial if an alternate method of production of carboxylic acids could be realized. Of particular interest would be a method that generates little, if any, formate ester.

FIG. 1

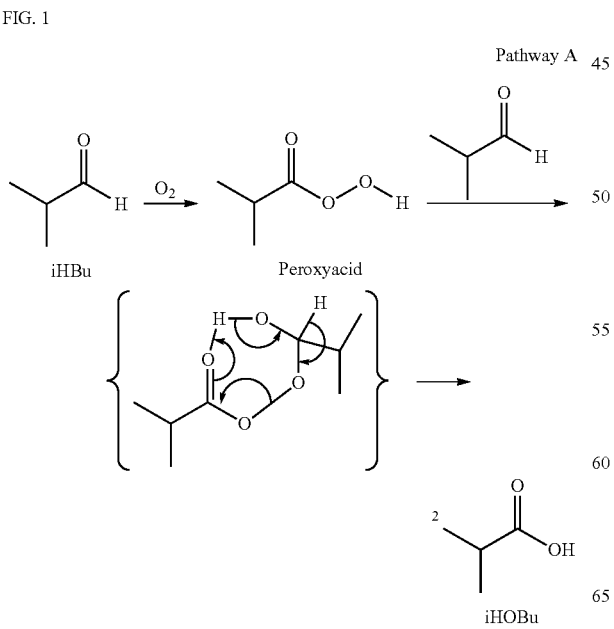

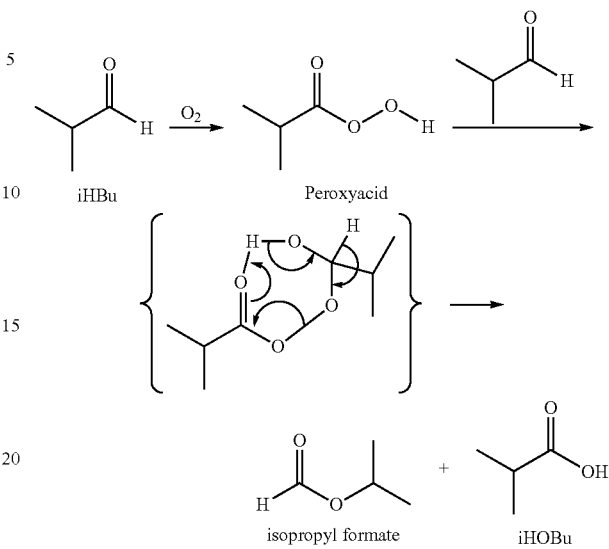

Esterification is a classical organic chemistry reaction in which a carboxylic acid and an alcohol combine in a condensation reaction, in the presence of an acid, to generate one mole of ester and one mole of water. The reaction is reversible, that is, in the presence of water and an acid catalyst, a mole of alcohol and a mole of carboxylic acid can be obtained from the ester. Hydrolysis of esters could be used to generate carboxylic acids, such as isobutyric acid, without co production of isopropyl formate byproduct.

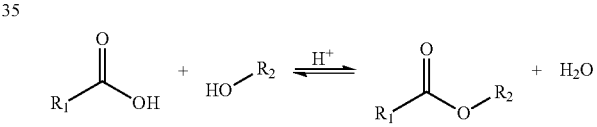

The production of carboxylic acids by oxidation of an aldehyde is thus plagued by low selectivity due to the formation of formate esters from the competing Bayer Villager mechanism. By first converting the aldehyde, or corresponding alcohol, to an ester, formate-free carboxylic acid can be obtained by catalytic hydrolysis of the ester. In such a reaction, we have surprisingly found that the addition of a homogenizing solvent improves the conversion and yield of the reaction.

SUMMARY OF THE INVENTION

In one aspect, the present invention relates to processes for preparing carboxylic acids from organic esters, the processes comprising contacting an ester with water in the presence of an acid catalyst and a homogenizing solvent at conditions effective to form a carboxylic acid. In a further aspect, the homogenizing solvent is present in an amount sufficient to form a single-phase reaction mixture comprising the ester, water, and homogenizing solvent. In another aspect, the homogenizing solvent is selected from acetonitrile, dimethyl sulfoxide, and 1,4-dioxane.

Further aspects of the invention are as disclosed and claimed herein.

DETAILED DESCRIPTION

In one aspect, the present invention is directed to processes for preparing carboxylic acids from organic esters, which include contacting an ester with water in the presence of an acid catalyst and a homogenizing solvent in a reaction mixture at conditions effective to form a carboxylic acid. According to the invention, the homogenizing solvent is present in the reaction mixture in an amount sufficient to form a single-phase reaction mixture comprising the ester, water, and homogenizing solvent. In an aspect, the homogenizing solvent is selected from acetonitrile, dimethyl sulfoxide, and 1,4-dioxane.

In another aspect, the ester corresponds to the formula $R_1COOR_2$, wherein $R_1$ is hydrogen or an aromatic or aliphatic alkyl having from 1 to 20 carbon atoms, and $R_2$ is an aromatic or aliphatic alkyl having from 1 to 20 carbon atoms. Alternatively, $R_1$ may hydrogen or an aromatic or aliphatic alkyl having from 1 to 6 carbon atoms, and $R_2$ an aromatic or aliphatic alkyl having from 1 to 6 carbon atoms.

In a further aspect, the ester may be selected from one or more of ethyl acetate, methyl propionate, ethyl propionate, propyl propionate, n-butyl propionate, 2-methyl-propyl propionate, pentyl propionate, isopentyl propionate, 2-methylbutyl propionate, hexyl propionate, heptyl propionate, octyl propionate, 2-ethyl-hexyl propionate, nonyl propionate, decyl propionate, 2-propyl-heptyl propionate, benzyl propionate, methyl butyrate, ethyl butyrate, propyl butyrate, n-butyl butyrate, 2-methyl-propyl butyrate, pentyl butyrate, isopentyl butyrate, 2-methylbutyl butyrate, hexyl butyrate, heptyl butyrate, octyl butyrate, 2-ethyl-hexyl butyrate, nonyl butyrate, decyl butyrate, 2-propyl-heptyl butyrate, benzyl butyrate, methyl isobutyrate, ethyl isobutyrate, propyl isobutyrate, n-butyl isobutyrate (NBIB), 2-methyl-propyl isobutyrate (isobutyl isobutyrate, IBIB), pentyl isobutyrate, isopentyl isobutyrate, 2-methylbutyl isobutyrate, hexyl isobutyrate, heptyl isobutyrate, octyl isobutyrate, 2-ethylhexyl isobutyrate, nonyl isobutyrate, decyl isobutyrate, 2-propyl-heptyl isobutyrate, benzyl isobutyrate, methyl pentanoate, ethyl pentanoate, propyl pentanoate, n-butyl pentanoate, 2-methyl-propyl pentanoate, pentyl pentanoate, isopentyl pentanoate, 2-methylbutyl pentanoate, hexyl pentanoate, heptyl pentanoate, octyl pentanoate, 2-ethylhexyl pentanoate, nonyl pentanoate, decyl pentanoate, 2-propyl-heptyl pentanoate, benzyl pentanoate, methyl hexanoate, ethyl hexanoate, propyl hexanoate, n-butyl hexanoate, 2-methyl-propyl hexanoate, pentyl hexanoate, isopentyl hexanoate, 2-methylbutyl hexanoate, hexyl hexanoate, heptyl hexanoate, octyl hexanoate, 2-ethyl-hexyl hexanoate, nonyl hexanoate, decyl hexanoate, 2-propylheptyl hexanoate, benzyl hexanoate, methyl 2-ethyl hexanoate, ethyl 2-ethyl hexanoate, propyl 2-ethyl hexanoate, butyl 2-ethylhexanoate, isobutyl 2-ethylhexanoate, pentyl 2-ethyl hexanoate, benzyl 2-ethylhexanoate, methyl 2-propyheptanoate, ethyl 2-propyheptanoate, propyl 2-propyheptanoate, n-butyl 2-propyheptanoate, 2-methyl-propyl 2-propyheptanoate, pentyl 2-propyheptanoate, isopentyl 2-propyheptanoate, 2-methylbutyl 2-propyheptanoate, hexyl 2-propyheptanoate, heptyl 2-propyheptanoate, octyl 2-propyheptanoate, 2-ethyl-hexyl 2-propyheptanoate, nonyl 2-propyheptanoate, decyl 2-propyheptanoate, 2-propyl-heptyl 2-propyheptanoate, benzyl 2-propyheptanoate, or benzyl benzoate.

In a specific embodiment, the ester comprises isobutyl isobutyrate and the homogenizing solvent comprises acetonitrile, or 1,4-dioxane, or dimethylsulfoxide. Further examples may include diglyme (diethylene glycol dimethyl ether) and dimethyl formamide (DMF).

In a further aspect, the acid catalyst comprises one or more of hydrochloric acid, sulfuric acid, nitric acid, p-tolyl sulfonic acid, hydrofluoric acid, or hydrobromic acid. And in another aspect, the acid catalyst is present in the reaction mixture in an amount from about 2% to about 5%.

According to another aspect, the reaction mixture may be at a temperature from about 50° C. to about 300° C., or from 100° C. to 150° C. In a further aspect, the reaction mixture is at a pressure from about 25 psig to about 500 psig, or from 100 psig to 300 psig.

Surprisingly, we have found according to the invention that to obtain high conversion of ester to carboxylic acid product, the reaction mixture should be homogeneous. Typically, a mixture of organic ester and water would be biphasic and the reaction would proceed slowly. By adding a homogenizing solvent, thus bringing water and ester into close contact in one phase, the reaction proceeds more quickly towards completion.

According to the invention, ester hydrolysis may be accomplished by contacting an organic ester with an aqueous solution of a strong acid catalyst in the presence of a homogenizing solvent. The reaction is an equilibrium reaction and will proceed to equilibrium concentrations as defined by the concentrations of the starting materials. The reaction can be driven towards completion either by having an excess of one starting material or by removing the low boiling product as it is formed. In practice, it is typically advantageous to have the lowest boiling starting material in excess or to run the reaction in such a way that the lowest boiling product, typically the alcohol, is removed from the reaction mixture.

It is noteworthy that reactions run with an excess of water relative to the starting ester proceed more quickly to the equilibrium point by incorporating a homogenizing solvent. Such a solvent brings both the aqueous and organic phases into contact and allows for quicker reaction. Any solvent that is not an alcohol or carboxylic acid and that allows for both the organic ester and water to be miscible is suitable for use according to the invention. Solvents applicable to this invention include acetone, acetonitrile, dimethyl sulfoxide, and 1,4-dioxane. Of particular interest are acetone and acetonitrile as their low boiling points allow for easy separation and recycle.

For the purposes of this invention, an ester is defined as any organic compound that may be formed from the condensation reaction of a carboxylic acid and an alcohol, and having the formula $R_1COOR_2$ where in $R_1$ and $R_2$ can be the same or different organic moieties, either aromatic or aliphatic, with $R_2$ possessing a carbon chain of 1 to 20 carbons, or 1 to 10 carbon atoms, or 1 to 6 carbon atoms, or 1 to 4 carbon atoms. Similarly, $R_1$ may possess a carbon chain of 1 to 20 carbons, or 1 to 10 carbon atoms, or 1 to 6 carbon atoms, or 1 to 4 carbon atoms, or may be hydrogen. These carbon chains may be the same or different or may be structural isomers of each other. Thus, while $R_1$ can be hydrogen, $R_2$ cannot be hydrogen.

Alternatively, the organic esters useful according to the invention may be formed by further processes, without limitation, including those further described below.

The organic esters useful in this invention are any that contain a carboxylic acid moiety of interest to the practitioner. In theory, any ester could be used. Of particular interest are ethyl acetate, methyl propionate, ethyl propionate, propyl propionate, n-butyl propionate, 2-methyl-propyl propionate, pentyl propionate, isopentyl propionate, 2-methylbutyl propionate, hexyl propionate, heptyl propionate, octyl propionate, 2-ethyl-hexyl propionate, nonyl propionate, decyl propionate, 2-propyl-heptyl propionate, benzyl propionate, methyl butyrate, ethyl butyrate, propyl butyrate, n-butyl butyrate, 2-methyl-propyl butyrate, pentyl butyrate, isopentyl butyrate, 2-methylbutyl butyrate, hexyl butyrate, heptyl butyrate, octyl butyrate, 2-ethyl-hexyl butyrate, nonyl butyrate, decyl butyrate, 2-propyl-heptyl butyrate, benzyl butyrate, methyl isobutyrate, ethyl isobutyrate, propyl isobutyrate, n-butyl isobutyrate (NBIB), 2-methyl-propyl isobutyrate (isobutyl isobutyrate, IBIB), pentyl isobutyrate, isopentyl isobutyrate, 2-methylbutyl isobutyrate, hexyl isobutyrate, heptyl isobutyrate, octyl isobutyrate, 2-ethylhexyl isobutyrate, nonyl isobutyrate, decyl isobutyrate, 2-propyl-heptyl isobutyrate, benzyl isobutyrate, methyl pentanoate, ethyl pentanoate, propyl pentanoate, n-butyl pentanoate, 2-methyl-propyl pentanoate, pentyl pentanoate, isopentyl pentanoate, 2-methylbutyl pentanoate, hexyl pentanoate, heptyl pentanoate, octyl pentanoate, 2-ethyl-hexyl pentanoate, nonyl pentanoate, decyl pentanoate, 2-propyl-heptyl pentanoate, benzyl pentanoate, methyl hexanoate, ethyl hexanoate, propyl hexanoate, n-butyl hexanoate, 2-methyl-propyl hexanoate, pentyl hexanoate, isopentyl hexanoate, 2-methylbutyl hexanoate, hexyl hexanoate, heptyl hexanoate, octyl hexanoate, 2-ethyl-hexyl hexanoate, nonyl hexanoate, decyl hexanoate, 2-propyl-heptyl hexanoate, benzyl hexanoate, methyl 2-ethyl hexanoate, ethyl 2-ethyl hexanoate, propyl 2-ethyl hexanoate, butyl 2-ethylhexanoate, isobutyl 2-ethylhexanoate, pentyl 2-ethyl hexanoate, benzyl 2-ethylhexanoate, methyl 2-propyheptanoate, ethyl 2-propyheptanoate, propyl 2-propyheptanoate, n-butyl 2-propyheptanoate, 2-methyl-propyl 2-propyheptanoate, pentyl 2-propyheptanoate, isopentyl 2-propyheptanoate, 2-methylbutyl 2-propyheptanoate, hexyl 2-propyheptanoate, heptyl 2-propyheptanoate, octyl 2-propyheptanoate, 2-ethyl-hexyl 2-propyheptanoate, nonyl 2-propyheptanoate, decyl 2-propyheptanoate, 2-propyl-heptyl 2-propyheptanoate, benzyl 2-propyheptanoate, and benzyl benzoate.

According to the invention, ester hydrolysis is expedited by addition of a catalytic amount of an acid. According to the invention, an acid includes any substance that, upon dissolution, will donate an $H^+$ ion to its conjugate base. Alternatively, any substance that upon dissolution in water will lower the pH of the water below 7 may also be categorized as an acid. In particular, substances having a pKa<2 will be an efficient catalyst for this invention. Strong acids such as hydrochloric acid, sulfuric acid, nitric acid, p-tolyl sulfonic acid, hydrofluoric acid, hydrobromic acid, and the like are all suitable catalysts for use according to the invention.

The acid catalyst according to the invention is fed into the reaction mixture, typically in a reactor, in such a way that the total concentration of acid in the reactor is typically held from about 2% to about 5%. More broadly, the invention may be carried out with any acid concentration from about 0.5% to about 50%, or from 1% to 10%. At concentrations below about 2%, the reactivity of the hydrolysis begins to slow down substantially.

According to the invention, the homogenizing solvent is present in the reaction mixture in an amount sufficient to form a single-phase reaction mixture comprising the ester, water, and homogenizing solvent. The amount of homogenizing solvent may thus vary widely and will differ based on the desired reaction and reaction conditions. When we say that the reaction mixture forms a single phase, we mean essentially that the reaction mixture appears visually to be a single phase, and that the desired reaction is thereby facilitated. No more precise definition of a single-phase system is necessary for purposes of practicing the invention. Those skilled in the art will readily be able to determine a suitable amount of homogenizing solvent to use in a given system. We do note that, for IBIS, the amount of homogenizing solvent typically is from 40-50% by weight of solvent relative to the entire reaction mixture.

The reaction can be run in any typical reactor set-up. Those skilled in the art can determine appropriate reactor schemes, but continuous stirred tanks, plug-flow reactors, or down flow trickle beds are examples. In an embodiment, the reaction is carried out in a continuous stirred tank reactor. Alternatively, the reaction is carried out in a batch process in any suitable vessel.

The reaction can be run at temperatures, for example, from about 50° C. to about 300° C., or from 60° C. to 200° C., or from 100° C. to 150° C. inclusively.

Pressure may be applied to the reactor, in order to keep the starting materials, products, and solvent in the liquid phase at the desired temperature. The reaction, therefore, can be run, for example at pressures from about 0 psig to about 1000 psig, or from 25 psig to 500 psig, or from 100 psig to 300 psig, and especially from 0 psig to 300 psig inclusively. In a particular embodiment, the reaction may be run at 200 psig. Pressure can be supplied, for example, by an inert gas such as nitrogen, argon, carbon dioxide, methane, or the like.

The product carboxylic acid can be separated from the reactor effluent by any typical means. Examples of such techniques include decantation, extraction, crystallization, evaporation, and distillation.

The organic ester used as a starting material can be generated by any means known in the art. For example, a Tischenko reaction could be used to generate isobutyl isobutyrate (IBIB) from isobutyraldehyde. In another example, the so-called Milstein catalyst could be used to generate IBIB from isobutanol. Still in another example, the so-called Shvo's catalyst could be used to generate methyl isobutyrate from methanol and isobutyraldehyde. In a particular embodiment of this invention, Milstein's catalyst is used to generate IBIB from isobutanol, the IBIB is converted to isobutyric acid and isobutanol, and the isobutanol is recovered by distillation and recycled to provide more IBIB.

The practice of this invention provides carboxylic acid products in higher selectivity than achieved through standard means of aldehyde oxidation. The invention produces a product stream containing little to no amount of formate esters.

The following examples set forth suitable and/or preferred methods and results in accordance with the invention. It is to be understood, however, that these examples are provided by way of illustration and nothing therein should be taken as a limitation upon the overall scope of the invention. All percentages are by weight unless otherwise specified.

Example 1 (Comparative)

A 100 mL glass three neck round bottom flask was charged with isobutyl isobutyrate (3.00 g, 12.8 mmol), 12.5 g of an aqueous 10% HCl solution (11.25 g $H_2O$, 625 mmol), and a magnetic stir bar. In this example, a homogenizing solvent was not used. The flask had a reflux condenser and a thermowell attached. The reaction apparatus was placed in an oil bath on an electric stirring/heating device. The reaction mixture was brought to reflux with stirring and held for 4 h. The reaction mixture was cooled and poured into a laboratory separatory funnel. The aqueous and organic layers were analyzed by GC. The aqueous layer (13.8 g) contained 93% water, 0.29% IBIB, 3.3% isobutanol, and 3.9% isobutyric acid. The organic layer (2.0 g) contained 92% IBIB, 1.1% water, 3.0% isobutanol, and 3.9% isobutyric acid. In sum, the reaction resulted in 38% conversion of IBIB and 32% yield of isobutyric acid.

Example 2 (Comparative)

A 100 mL stainless steel autoclave was charged with IBIB (16.0 g, 111 mmol) and 48.1 g of an aqueous 10% para-tolyl sulfonic acid solution (43.3 g H2O, 2405 mmol). In this example, a homogenizing solvent was not used. The autoclave was sealed and brought to 100° C. The autoclave was brought to 200 psig with $N_2$ and held with stirring for 4 h. After 4 h, the autoclave was cooled and the reaction mixture poured into a laboratory separatory funnel. The aqueous and organic layers were analyzed by GC. The aqueous layer (47.8 g) contained 94% water, 1.6% IBIB, 1.6% isobutanol, and 2.1% isobutyric acid. The organic layer (14.9 g) contained 79% IBIB, 6.4% water, 6.9% isobutanol, and 7.9% isobutyric acid. In sum, the reaction resulted in 22% conversion of IBIB and 22% yield of isobutyric acid.

Example 3

A 250 mL glass three neck round bottom flask was charged with isobutyl isobutyrate (25.1 g, 174 mmol), 72.5 g of an aqueous 10% HCl solution (65.3 g H₂O, 3625 mmol), and a magnetic stir bar. Acetonitrile ($CH_3CN$) was added until a homogeneous solution was obtained (86.8 g was added). The flask had a reflux condenser and a thermowell attached. The reaction apparatus was placed in an oil bath on an electric stirring/heating device. The reaction mixture was brought to reflux with stirring and held for 4 h. The reaction mixture was cooled and analyzed by GC. The reaction product (183 g) contained 46% $CH_3CN$, 5.1% IBIB, 39% water, 3.9% isobutanol, and 5.3% isobutyric acid. In sum, the reaction resulted in 63% conversion of IBIB and 64% yield of isobutyric acid.

Example 4

A 250 mL glass three neck round bottom flask was charged with isobutyl isobutyrate (20.0 g, 139 mmol), 70.0 g of an aqueous 10% HCl solution (63.0 g H₂O, 3500 mmol), and a magnetic stir bar. Acetone was added until a homogeneous solution was obtained (135 g is added). The flask had a reflux condenser and a thermowell attached. The reaction apparatus was placed in an oil bath on an electric stirring/heating device. The reaction mixture was brought to reflux with stirring and held for 4 h. The reaction mixture was cooled and analyzed by GC. The reaction product (220 g) contained 60% acetone, 1.1% IBIB, 29% water, 4.7% isobutanol, and 4.8% isobutyric acid. In sum, the reaction resulted in 88% conversion of IBIB and 87% yield of isobutyric acid.

Examples 5-7

These examples were repeated in the same fashion as Example 4; however, the mol:mol ratio of H2O:IBIB was varied as indicated in Table 1.

Example 8 (Comparative)

A 250 mL glass three neck round bottom flask was charged with isobutyl isobutyrate (20.6 g, 143 mmol), 71.2 g of an aqueous 10% HCl solution (64 g H₂O, 3560 mmol), tetrabutylammonium chloride (3.31 g, 12 mmol) as a phase transfer catalyst, and a magnetic stir bar. In this example, a homogenizing solvent was not used. The flask had a reflux condenser and a thermowell attached. The reaction apparatus was placed in an oil bath on an electric stirring/heating device. The reaction mixture was brought to reflux with stirring and held for 4 h. The reaction mixture was cooled and poured into a laboratory separatory funnel. The aqueous and organic layers were analyzed by GC. The aqueous layer (73.9 g) contained 93% water, 4.1% IBIB, 1.3% isobutanol, and 1.8% isobutyric acid. The organic layer (18.0 g) contained 62% IBIB, 5.2% water, 15% isobutanol, and 18% isobutyric acid. In sum, the reaction resulted in 38% conversion of IBIB and 32% yield of isobutyric acid.

Example 9

A 50 mL glass three neck round bottom flask was charged with isobutyl isobutyrate (2.00 g, 13.9 mmol), 7.4 g of an aqueous 5% HCl solution (7 g H₂O, 389 mmol), and a magnetic stir bar. Acetone was added until a homogeneous solution was obtained (13 g is added). The flask had a reflux condenser and a thermowell attached. The reaction apparatus was placed in an oil bath on an electric stirring/heating device. The reaction mixture was brought to reflux with stirring and held for 4 h. The reaction mixture was cooled and analyzed by GC. The reaction mixture (21.5 g) contained 59% acetone, 6.8% IBIB, 31% water, 1.5% isobutanol, and 1.6% isobutyric acid. In sum, the reaction resulted in 27% conversion of IBIB and 28% yield of isobutyric acid.

Example 10

A 100 mL stainless steel autoclave was charged with IBIB (8.1 g, 56.4 mmol), 24.1 g of an aqueous 10% para-tolyl sulfonic acid solution (21.7 g H2O, 1206 mmol), and 45 g of acetone. The autoclave was sealed and brought to 100° C. The autoclave was brought to 200 psig with $N_2$ and held with stirring for 4 h. After 4 h, the autoclave was cooled and the reaction mixture analyzed by GC. The reaction mixture contained 59% acetone, 30% water, 2.4% IBIB, 3.9% isobutanol, and 4.6% isobutyric acid. In sum, the reaction resulted in 77% conversion of IBIB and 71% yield of isobutyric acid.

Example 11-14

Examples 11-14 were conducted in similar manner to Example 10 except the $H_2O$:IBIB ratio or the temperature or pressure were changed as indicated in Table 2.

TABLE 1

| Example# | mol H2O:mol IBIB | % Acetone | % IBIB | % H2O | % iBuOH | % iHOBu | Conversion | Yield |
| --- | --- | --- | --- | --- | --- | --- | --- | --- |
| 4 | 28 | 60% | 1.1% | 29% | 4.7% | 4.8% | 88% | 87% |
| 5 | 10 | 61% | 5.8% | 21% | 5.3% | 6.6% | 67% | 61% |
| 6 | 13 | 63% | 4.4% | 22% | 4.9% | 5.3% | 68% | 64% |
| 7 | 16 | 58% | 4.5% | 27% | 5.0% | 5.9% | 68% | 68% |

TABLE 2

| Example | H2O:IBIB | Temperature (° C.) | Pressure (psig) | IBIB Conversion | iHOBu Selectivity |
|---|---|---|---|---|---|
| 10 | 23.7 | 100.00 | 200.00 | 77% | 71% |
| 11 | 13.3 | 100.00 | 200.00 | 71% | 74% |
| 12 | 7.9 | 100.00 | 200.00 | 67% | 69% |
| 13 | 7.9 | 150.00 | 200.00 | 79% | 81% |
| 14 | 7.9 | 100.00 | 300.00 | 66% | 67% |

Example 15 (Comparative)

A 100 mL stainless steel autoclave was charged with IBIB (10 g, 69 mmol), 31.7 g of an aqueous 10% para-tolyl sulfonic acid solution (28.5 g H2O, 1585 mmol), and tetrabutylammonium chloride (1.7 g, 6 mmol) as a phase transfer catalyst. In this example, a homogenizing solvent was not used. The autoclave was sealed and brought to 100° C. The autoclave was brought to 200 psig with $N_2$ and held with stirring for 4 h. After 4 h, the autoclave was cooled and the reaction mixture poured into a laboratory separatory funnel. The aqueous and organic layers were analyzed by GC. The aqueous layer (31.4 g) contained 94% water, 0.04% IBIB, 2.9% isobutanol, and 3.1% isobutyric acid. The organic layer (10.5 g) contained 50% IBIB, 14% water, 16% isobutanol, and 19% isobutyric acid. In sum, the reaction resulted in 48% conversion of IBIB and 48% yield of isobutyric acid.

Example 16

A 300 ml stainless steel autoclave was modified in such a way that it became a continuous stirred tank reactor. A IPSCO brand electric syringe pump was used to feed a mixture of 20% IBIB, 20% aqueous p-toyl sulfonic acid solution (10% acid), and 60% acetone at a constant feed rate of 1.5 mL/min. An internal dip tube was used to hold the volume in the reactor constant at 150 mL. The liquid overflow from the dip tube passed through a dome back pressure regulator that was set to hold the pressure at 200 psig in the reactor. Constant pressure was maintained with a Brooks mass flow controller that sends a steady stream of $N_2$ into the reactor at 50 SCCM. The reactor was held in an electric heating mantle that maintained temperature at 100° C. and an overhead electric stirring motor that maintained an internal stirring impeller at 600 rpm. Under these conditions, over a 4 h period, an IBIB conversion of 31% was obtained with an iHOBu yield of 32%.

Examples 17-25

The apparatus described in Example 16 was used with varying amounts of water and IBIB or at various feed rates as described in Table 3.

Example 26

The CSTR described in Example 14 was utilized. The feed mixture consisted of 20% IBIB, 20% aqueous phosphoric acid solution (10% H3PO4), and 60% acetone. The mixture was fed continuously over 4 h at 1.0 mL/min. The reactor was maintained at 100° C. and 200 psig. An IBIB conversion of 15% was obtained with an iHOBu yield of 12%.

Example 27

The CSTR described in Example 14 was utilized. The feed mixture consisted of 16% methyl isobutyrate, 40% aqueous p-tolyl sulfonic acid solution (10% PTSA), and 44% acetone. The mixture was fed continuously over 4 h at 0.5 mL/min. The reactor was maintained at 100° C. and 200 psig. The overflow product had an average composition of 43% acetone, 40% water, 11% isobutyric acid, 4% methyl isobutyrate, and 2% methanol. Methyl isobutyrate conversion was 75% and isobutyric acid yield was 72%.

Example 28

The CSTR described in Example 14 was utilized. The feed mixture consisted of 11% methyl 2-ethylhexanoate, 24% aqueous p-tolyl sulfonic acid solution (10% PTSA), and 65% acetone. The mixture was fed continuously over 4 h at 0.5 mL/min. The reactor was maintained at 100° C. and 200 psig. The overflow product had an average composition of 67% acetone, 24% water, 7% 2-ethylhexanoic acid, 0.8% methyl 2-ethylhexanoate, and 1% methanol. Methyl 2-ethylhexanoate conversion was 93% and 2-ethylhexanoic acid yield was 98%.

Examples 29-31

In this example, Example 3 was repeated but with different solvents: DMSO, 1,4-dioxane, and THF. Results are shown in Table 4. We note that the THF did not serve as a homogenizing solvent in this reaction.

TABLE 3

| Example | mols IBIB | mols H2O | % acid | H2O:IBIB | Temp (° C.) | Pressure (psig) | Feed Rate (mL/min) | Conversion | Yield |
|---|---|---|---|---|---|---|---|---|---|
| 16 | 0.366 | 2.93 | 10% | 8.0 | 100 | 200 | 1.5 | 31% | 32% |
| 17 | 0.524 | 4.19 | 10% | 8.0 | 100 | 200 | 1.5 | 38% | 37% |
| 18 | 0.351 | 2.81 | 10% | 8.0 | 100 | 200 | 1.0 | 42% | 44% |
| 19 | 0.171 | 1.37 | 10% | 8.0 | 100 | 200 | 0.5 | 47% | 45% |
| 20 | 0.194 | 2.72 | 10% | 14.0 | 100 | 200 | 1.0 | 57% | 58% |
| 21 | 0.119 | 1.67 | 10% | 14.0 | 100 | 200 | 0.5 | 65% | 60% |
| 22 | 0.059 | 0.82 | 10% | 13.9 | 100 | 200 | 0.25 | 71% | 69% |
| 23 | 0.245 | 3.43 | 10% | 14.0 | 150 | 200 | 1.0 | 82% | 80% |
| 24 | 0.078 | 4.35 | 10% | 55.8 | 100 | 200 | 1.0 | 81% | 79% |
| 25 | 0.247 | 1.98 | 5% | 8.0 | 100 | 200 | 1.0 | 29% | 28% |

TABLE 4

| Example# | Solvent | % Solvent | % IBIB | % H2O | % iBuOH | % iHOBu | Conversion | Yield |
|---|---|---|---|---|---|---|---|---|
| 29 | DMSO | 56% | 4.1% | 31% | 4.3% | 4.5% | 66% | 62% |
| 30 | 1,4-dioxane | 52% | 2.8% | 31% | 5.1% | 5.9% | 78% | 77% |
| 31 | THF | 46% | 13% | 39% | 1.1% | 1.1% | 14% | 12% |
| 3 | CH3CN | 46% | 1.1% | 29% | 3.9% | 5.3% | 63% | 64% |

The foregoing description of various embodiments of the invention has been presented for purposes of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

That which is claimed is:

1. A process for preparing a carboxylic acid from an organic ester, the process comprising:
    contacting an ester with water in the presence of an acid catalyst and a homogenizing solvent in a reaction mixture at conditions effective to form a carboxylic acid,
    wherein the homogenizing solvent is present in the reaction mixture in an amount sufficient to form a single-phase reaction mixture comprising the ester, water, and homogenizing solvent, and
    wherein the homogenizing solvent is selected from acetonitrile, dimethyl sulfoxide, and 1,4-dioxane; wherein the ester comprises isobutyl isobutyrate and the homogenizing solvent comprises acetonitrile.

2. The process of claim 1, further comprising a step of removing a lower boiling product from the reaction mixture.

3. The process of claim 2, wherein the lower boiling product is an alcohol.

4. The process of claim 1, wherein the ester corresponds to the formula $R_1COOR_2$, wherein $R_1$ is hydrogen or an aromatic or aliphatic alkyl having from 1 to 20 carbon atoms, and $R_2$ is an aromatic or aliphatic alkyl having from 1 to 20 carbon atoms.

5. The process of claim 1, wherein the ester corresponds to the formula $R_1COOR_2$, wherein $R_1$ is hydrogen or an aromatic or aliphatic alkyl having from 1 to 6 carbon atoms, and $R_2$ is an aromatic or aliphatic alkyl having from 1 to 6 carbon atoms.

6. The process of claim 1, wherein the homogenizing solvent further comprises 1,4-dioxane.

7. The process of claim 1, wherein the homogenizing solvent further comprises dimethylsulfoxide.

8. The process of claim 1, wherein the acid catalyst comprises one or more of hydrochloric acid, sulfuric acid, nitric acid, p-tolyl sulfonic acid, hydrofluoric acid, or hydrobromic acid.

9. The process of claim 1, wherein the reaction mixture is at a temperature from about 50° C. to about 300° C.

10. The process of claim 1, wherein the reaction mixture is at a temperature from about 100° C. to about 150° C.

11. The process of claim 1, wherein the reaction mixture is at a pressure from about 25 psig to about 500 psig.

12. The process of claim 1, wherein the reaction mixture is at a pressure from 100 psig to 300 psig.

* * * * *